(12) United States Patent
Scotland et al.

(10) Patent No.: US 9,333,165 B1
(45) Date of Patent: May 10, 2016

(54) CREAM TO POWDER COSMETIC COMPOSITIONS

(71) Applicant: L'OREAL, Paris (FR)

(72) Inventors: Shauna-Kaye Lecaine Dominique Scotland, Morristown, NJ (US); Balanda Atis, Newark, NJ (US); Debra Joy Coleman-Nally, Hillsborough, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/564,157

(22) Filed: Dec. 9, 2014

(51) Int. Cl.
| | |
|---|---|
| *A61K 8/92* | (2006.01) |
| *A61K 8/73* | (2006.01) |
| *A61K 8/37* | (2006.01) |
| *A61K 8/891* | (2006.01) |
| *A61K 8/19* | (2006.01) |
| *A61Q 1/02* | (2006.01) |
| *A61K 8/81* | (2006.01) |
| *A61K 8/88* | (2006.01) |

(52) U.S. Cl.
CPC . *A61K 8/927* (2013.01); *A61K 8/19* (2013.01); *A61K 8/37* (2013.01); *A61K 8/732* (2013.01); *A61K 8/8141* (2013.01); *A61K 8/88* (2013.01); *A61K 8/891* (2013.01); *A61K 8/92* (2013.01); *A61Q 1/02* (2013.01); *A61K 2800/43* (2013.01); *A61K 2800/594* (2013.01)

(58) Field of Classification Search
None
See application file for complete search history.

(56) References Cited

U.S. PATENT DOCUMENTS

| | | |
|---|---|---|
| 4,804,719 A | 2/1989 | Weaver et al. |
| 4,999,418 A | 3/1991 | Krutak et al. |
| 5,030,708 A | 7/1991 | Krutak et al. |
| 5,032,670 A | 7/1991 | Parham et al. |
| 5,043,376 A | 8/1991 | Sharma et al. |
| 5,102,980 A | 4/1992 | Krutak et al. |
| 5,104,913 A | 4/1992 | Sharma et al. |
| 5,106,942 A | 4/1992 | Krutak et al. |
| 5,143,722 A | 9/1992 | Hollenberg et al. |
| 5,194,463 A | 3/1993 | Krutak et al. |
| 5,281,659 A | 1/1994 | Weaver et al. |
| 6,294,180 B1 | 9/2001 | Demars et al. |
| 6,416,751 B1 | 7/2002 | Roulier et al. |
| RE38,441 E | 2/2004 | Jacks et al. |
| 7,250,156 B2 | 7/2007 | Vernaire et al. |
| 2002/0018791 A1 | 2/2002 | Vatter et al. |
| 2003/0219391 A1* | 11/2003 | Liew ............... A61K 8/26 424/59 |
| 2012/0276029 A1 | 11/2012 | Ascione et al. |
| 2014/0227213 A1 | 8/2014 | Scotland et al. |

FOREIGN PATENT DOCUMENTS

| | | |
|---|---|---|
| EP | 0747036 A2 | 12/1996 |
| EP | 1086683 A1 | 3/2001 |
| FR | 2792190 A1 | 10/2000 |
| WO | 9207913 A1 | 5/1992 |
| WO | 0074643 A1 | 12/2000 |
| WO | 0107007 A1 | 2/2001 |

OTHER PUBLICATIONS

Black|Up Paris, Oil Free Creme to Powder Foundation, Packaging, www.balckup.com, 75116 Paris.

* cited by examiner

*Primary Examiner* — Michael B Pallay
(74) *Attorney, Agent, or Firm* — Oblon, McClelland, Maier & Neustadt, L.L.P.

(57) ABSTRACT

Cosmetic compositions comprise, (a) at least one aluminum-based starch, (b) at least one aluminum-based starch/(meth) acrylates polymer blend, (c) at least one polymeric filler, (d) at least one liquid fatty ester, (e) at least one silicone solvent, (f) at least one wax having a melting point greater than or equal to 70° C., (g) at least one wax having a melting point less than 70° C., (h) a coloring agent, and (i) optionally a filler other than (c); wherein the total amount of waxes ((f)+(g)) is less than about 5%. Methods for making up and/or enhancing the appearance of a keratinous substrate, such as the skin, comprise applying said compositions to the keratinous substrate, and included is a method of making the compositions.

25 Claims, No Drawings

CREAM TO POWDER COSMETIC COMPOSITIONS

TECHNICAL FIELD

The present invention relates to an anhydrous, hot pour, cosmetic composition having low wax levels and which transitions from a crème to a powder texture upon application to a keratinous substrate. Cosmetic compositions according to the invention impart true color, while also reducing dullness, whiteness, and/or ashiness of the keratinous substrate, in particular skin. These compositions are particularly useful as foundations for deeper (darker) skin tones.

BACKGROUND OF THE INVENTION

Foundations are known and used in the cosmetic field to impart even color to the skin. It is also known that foundations can help to control oil and shine on the skin. However, when preparing foundations for deeper ethnic skin tones, and especially in the case of oil-absorbing and/or matte compositions, it has been found that such compositions tend to impart an undesirable, dull or ashy hue to darker skin.

Polymeric and mineral fillers as well as starches are well-known in the cosmetic field. Such fillers and starches are generally incorporated into cosmetic compositions as oil-absorptive components which tend to have good adherence to the skin and contribute to the matte properties of the compositions. However, the use of fillers and starches in compositions can tend to give the user an undesirable ashy and/or dull appearance and may, in some cases, result in a dry skin feel. Moreover, the amount of fillers/starch necessary to adequately absorb oil and prevent shine generally also tends to whiten the formulation and give the ashy dull hue that becomes more apparent after the composition dries on the skin. This problem is greatly exacerbated in the case of foundations for women with deeper ethnic skin tones.

Currently available hot pour foundations typically include high levels of waxes. This results in a hard powder texture that has relatively poor product pick up and poor coverage. In addition, these high wax foundations tend to be dull and do not provide natural skin tone. This is because the waxes tend to opacify and thereby whiten the base composition muting the effect of the colorants and resulting in an unnatural skin tone or shade.

Thus, there remains a need in the cosmetic industry to provide consumers having deeper ethnic skin tones with cosmetic products having improved properties such as improved oil absorption, shine reduction, wear of mattity, matte, texture, long-wear properties, and/or ability to impart true color, while also reducing dullness, whiteness, and/or ashiness of the skin.

The current composition has a high powder load providing enhanced oil absorption and shine control, and also reduced amount of waxes permitting more natural skin tone and shade. The compositions have a rich, non-drying crème texture that affords good product pick up and coverage, and quickly transitions to a powder upon application to the skin retaining oil and shine control properties.

By high powder load, it is meant that the compositions contain greater than about 30% of starches and other powders and that the ratio of all of the powders (including pigments, if they are powdered) to the solvents is greater than 1:1.

SUMMARY OF THE INVENTION

The invention relates to an anhydrous cosmetic composition comprising (a) at least one aluminum-based starch, (b) at least one aluminum-based starch and (met)acrylates polymer blend, (c) at least one polymeric filler, (d) at least one liquid fatty ester, (e) at least one silicone solvent, (f) at least one wax having a melting point greater than or equal to about 70° C., (g) at least one wax having a melting point less than about 70° C., (h) a coloring agent, and (i) optionally a filler other than (c), wherein the total amount of waxes ((f)+(g)) is less than about 5%.

The present invention further relates to methods for making up a keratinous substrate, preferably skin, comprising applying to the skin a composition according to the invention.

The present invention also relates to a method of making compositions according to the invention.

It is to be understood that both the foregoing general description and the following detailed description are exemplary and explanatory only, and are not restrictive of the invention.

DETAILED DESCRIPTION OF THE INVENTION

The cosmetic compositions of the invention are anhydrous, contain low amount of waxes (less than about 5%) and have a high powder load (greater than 30% total powders). These compositions provide a unique texture in that they are initially creamy, affording good spreadability (increased product pick up and coverage) and also feel less drying. They transition quickly to powder texture upon application providing good shine and oil control. The compositions impart true color while reducing the appearance of ashiness, whiteness, and/or dullness of the skin, which is especially useful for individuals having deeper ethnic skin tones. These compositions are capable of being hot poured at a temperature of 75-80° C.

In the following description of the invention and the claims appended hereto, it is to be understood that the terms used have their ordinary and accustomed meanings in the art, unless otherwise specified.

It is also to be understood that, as used herein the terms "the," "a," or "an," mean "at least one," and should not be limited to "only one" unless explicitly indicated to the contrary. Thus, for example, the use of "a siloxane resin" is intended to mean at least one siloxane resin.

"About" as used herein means within 10% of the indicated number (e.g. "about 10%" means 9%-11% and "about 2%" means 1.8%-2.2%).

The terms "ashy," "ashiness" and variations thereof are intended to refer to the appearance of a gray overcast on the skin or keratinous substrate after the product has been applied and evaluated after drying.

The term "deeper ethnic skin tones" is intended to refer to those skin tones that are darker and tend to have more pronounced and deeper red, red/yellow, and yellow undertones. Users with deeper ethnic skin tones may belong to ethnicities including, but not limited to, African, African-American, Caribbean, Hispanic, Middle Eastern, and Indian ethnicities.

"Free" or "devoid" means that while it is preferred that no amount of the specific component be present in the composition, it is possible to have very small amounts of it in the compositions of the invention provided that these amounts do not materially affect at least one, preferably most, of the advantageous properties of the compositions of the invention. Thus, for example, "free of X" means that X is preferably omitted (that is 0% by weight), but can be present in the composition at an amount of less than about 0.25% by weight, typically less than about 0.1% by weight, typically less than about 0.05% by weight, based on the total weight of the composition as a whole.

"Hot pour" or "capable of being hot poured" means that the compositions are heated to mix the various components and are soft and pourable at the given temperature (e.g. 75-80° C.), and then solidify upon cooling below this temperature. A composition that is capable of being hot poured enables the pouring of the composition into a mold for shaping and yet retain formula stability.

"Matte", as used in foundation means that the composition is not shiny, shimmery or wet looking. Rather, it is powdery looking. "Good wear of mattity" or "mattity" refers to a product/composition's ability to maintain a matte skin appearance and/or feel throughout a period of time, such as a day or the consumer's normal wear time for the product.

The term "true color" is intended to refer to a color or shade that is most accurate or closest to the tone of the keratinous substrate to which it is applied. For instance, in at least certain exemplary embodiments, a composition that imparts true color according to the disclosure closely matches the skin tone without leaving an ashy, dull, white, and/or gray appearance. True color refers to the color obtained not only upon application to the keratinous substrate, but also after drying.

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

Unless otherwise specified herein, all percentages and ratios of components are by weight relative to the total weight of the final composition.

In an embodiment, the invention relates to an anhydrous cosmetic composition comprising:
(a) at least one aluminum-based starch;
(b) at least one aluminum-based starch and (met)acrylates polymer blend;
(c) at least one polymeric filler;
(d) at least one liquid fatty ester;
(e) at least one silicone solvent;
(f) at least one wax having a melting point greater than or equal to about 70° C.;
(g) at least one wax having a melting point less than about 70° C. and being softer than (f);
(h) at least one coloring agent; and
(i) optionally a filler other than (c);
wherein the total amount of waxes ((f)+(g)) is less than about 5%, by weight, relative to the total weight of the composition.

In an embodiment, the amount of wax is less than about 4% by weight, typically less than about 3%, by weight, relative to the weight of the composition.

In another embodiment, the powder load (total amount of powders, including starches, polymeric filler, etc.) is greater than about 30% by weight.

In another embodiment, the amount of the aluminum-based starch (a) together with the aluminum-based starch and (met)acrylates polymer blend (b) is greater than about 20% [(a)+(b)>20%].

In another embodiment, the amount of the aluminum-based starch and (met)acrylates polymer blend is less than about 1.5%, by weight, relative to the weight of the composition.

In another embodiment, the ratio of the total amount of starch (a) and starch/(met)acrylates blend (b) to total amount of waxes ([(a)+(b)/(f)+(g)] is from about 15:1 to about 9:1, including all ranges and sub-ranges therebetween, including about from about 13:1 to about 10:1, including in particular about from about 12:1 to about 11:1

In an embodiment, the invention relates to an anhydrous cosmetic composition comprising:
(a) from about 20% to about 35%, by weight, of at least one aluminum-based starch;
(b) from about 0.1% to about 2%, by weight, at least one aluminum-based starch and (met)acrylates polymer blend;
(c) from about 0.5% to about 6%, by weight, of at least one polymeric filler;
(d) from about 2% to about 15%, by weight, at least one fatty ester;
(e) from about 20% to about 40%, by weight, at least one silicone solvent;
(f) less than or equal to about 1%, by weight, of at least one wax having a melting point greater than or equal to about 70° C.;
(g) from about 0.5% to about 2.5%, by weight, of at least one wax having a melting point less than about 70° C. and being softer than (f);
(h) at least one coloring agent; and
(i) optionally a mineral filler other than (c);
wherein the total amount of waxes ((f)+(g)) is less than about 3% by weight, the total amount of starch (a) and blend (b) is greater than about 20%, and ratio of amount of starch (a) plus blend (b) to the amount of waxes is from about 12:1 to about 11:1; all weights and ratios being relative to the total weight of the composition.

In a particular embodiment the aluminum-based starch (a) is a modified starch.

In any and all of the foregoing embodiments, the composition may further comprise emollients, preservatives, neutralizers, vitamins, additional fillers and the like. When present, those compounds comprise from about 0.1% to about 20% by weight, based on the total weight of the composition.

In another embodiment, the invention is also directed to a cosmetic process for making up and/or enhancing the appearance of a keratinous substrate, in particular skin, by applying to the skin a cosmetic composition according to the invention. This process may be used for oil and shine control, color/tone correction, and/or overall improved skin appearance.

Another embodiment of the invention is a container comprising the above described cosmetic composition.

Another embodiment of the invention is a method of making the above described cosmetic composition such as to minimize the formation of clumps. This process comprises making a slurry of a majority of the aluminum-based starch and the aluminum-based starch and (met)acrylates copolymer blend.

Aluminum-Based Starch (a)

The compositions of the invention include an aluminum-based starch. Preferably, the starch is a modified starch.

Modified starches are generally described in Kirk-Othmer Encyclopedia of Chemical Technology, Fourth Edition, Volume 22, pp. 699-719. Modified starches useful in cosmetics are also described in U.S. Pat. No. 6,294,180 and U.S. Pat. No. 6,416,751, incorporated herein by reference.

Non-limiting examples of aluminum-based modified starches that can be used in the invention include starches esterified with octenylsuccinic anhydride, and particularly aluminum starch octenyl succinate, such as the products under the tradenames Natrosorb® W and Natrosorb® HFW, and DryFlo, such as DryFlo® PC, DryFlo® plus and Dry-Flo® AF pure (all from Akzo Nobel (National Starch)), as well as the product Agenaflo® OS 9051 from Agrana Starch.

The aluminum-based starch is present in the compositions of the invention in amounts generally ranging from about 20%% to about 35% by weight, typically from about 22% to about 33% by weight, more typically from about 25% to about 30% by we, weight, based on the total weight of the composition, including all ranges and subranges in between.

Aluminum-Based Starch and (Met)Acrylates Polymer Blend (b)

The compositions of the invention include a blend of an aluminum-based starch and (met)acrylates polymer. As used herein, "(meth)acrylates" means methacrylate polymer or acrylate polymer.

Preferably, the aluminum-based starch and (met)acrylates polymer blend has an oil absorption greater than about 200 ml/100 g, typically greater than about 250 ml/100 g, more typically equal to or greater than about 300 ml/100 g. A non-limiting example of such a blend is aluminum starch octenylsuccinate (and) acrylates copolymer (and) magnesium carbonate, such as the product Natrosorb® HFB available from Akzo Nobel/National Starch (absorption of 303.73 ml/100 g).

The aluminum-based starch and (met)acrylates polymer blend (b) is present in the compositions of the invention in amounts generally ranging from about 0.1%% to about 1% by weight, typically from about 0.5% to about %1.5 by weight, more typically from about 0.8% to about 1.2% by weight, based on the total weight of the composition, including all ranges and subranges in between.

The cosmetic compositions of the invention are unique in containing high amounts of powders. Thus, in an embodiment, the amount of starch (a) plus starch/polymer blend (b) is greater than about 20%, more typically greater than 25%, most typically greater than 28%, by weight, based on the weight of the compositions, including all ranges and subranges in between.

Polymeric Filler (c)

The compositions of the invention include at least one polymeric filler other than starch (a) or polymer (b).

Useful polymeric fillers can include, for example, lamellar or nonlamellar, colorless or white polymeric particles. In certain embodiments, the polymeric filler may be chosen from polyamide powders, such as Nylon® or Orgasol® powders from Arkema; cellulose poly-β-alanine and polyethylene powders; tetrafluoroethylene polymer powders, such as Teflon® powders; lauroyllysine; polymeric hollow microspheres such as those of polyvinylidene chloride/acrylonitrile, for instance Expancel® from Nobel Industries; silicone resin microbeads, such as Tospearls® from Toshiba; elastomeric polyorganosiloxane particles, such as those obtained by polymerization of organopolysiloxane having at least two hydrogen atoms each bonded to a silicon atom and of an organopolysiloxane comprising at least two ethylenically unsaturated groups, for instance, two vinyl groups, in the presence of a platinum catalyst; and metal soaps derived from organic carboxylic acids comprising from 8 to 22 carbon atoms, such as from 12 to 18 carbon atoms, for example, zinc stearate, magnesium stearate, lithium stearate, zinc laurate, and magnesium myristate.

Silicone elastomer powders are also useful polymeric fillers. These powders include, but are not limited to, the powders sold under the names Trefil® Powder E-505C and Trefil® Powder E-506C by Dow Corning.

Acrylic polymer powders may also be used as fillers. Such powders include methacrylate polymers, for example methyl methacrylate/glycol dimethacrylate crosspolymer, methyl methacrylate crosspolymer, polymethyl methacrylate powders, polymethyl methacrylate/ethylene glycol dimethacrylate powders, polyallyl methacrylate/ethylene glycol dimethacrylate powders, and ethylene glycol dimethacrylate/lauryl methacrylate copolymer powders, and mixtures thereof.

Commercial examples of acrylic polymer powder products include methacrylate polymers such as polymethyl methacrylate powders sold under the name Covabead® LH85 by Wacker, DSPCS-12 series and SPCAT-12 from Kobo, Poly-Pore 200 series from Amcol, and Techpolymer MBP-8 (methyl methacrylated crosspolymer) from Sekisui Plastics; the polymethyl methacrylate/ethylene glycol dimethacrylate powders sold under the names Microsponge® 5640 Skin Oil Adsorber (methyl methacrylate/glycol dimethacrylate crosspolymer, Dow Corning) and Ganzpearl® GMP-0820 (Ganz Chemical); the polyallyl methacrylate/ethylene glycol dimethacrylate powders sold under the name Poly-Pore® L200 and Poly-Pore® E200 (Amcol); and acrylic acid copolymers available from Dow Corning/Enhanced Derm Technologies under the name Polytrap® (for example ethylene glycol dimethacrylate/lauryl methacrylate copolymer powder, sold under the name Polytrap® 6603).

Examples of suitable acrylic polymer powders are provide in US2002/018791, and US 2014/227213.

Preferably, the polymeric filler has an oil absorption greater than about 70 ml/100 g.

In at least one exemplary embodiment, the at least one polymeric filler is a polyamide powder selected from "Nylon-12" (CFTA name) (such as the product Orgasol 2002 EXD from Arkema/Atochem), "Nylon-6" (such as the product Orgasol, Arkema/Atochem), and mixtures thereof. These polyamides are also known according to their various physicochemical properties under the name "polyamide 12" and "polyamide 6". The polymeric filler preferably may also be selected from polymethyl methacrylate powders, such as Techpolymer MBP-8 (methyl methacrylated crosspolymer), from Sekisui Plastics. Mixtures of the polyamide powder and polymethyl methacrylate powder fillers may also be used.

The at least one polymeric filler may, in various exemplary embodiments, be present in the cosmetic compositions in an amount ranging from about 0.5% to about 6% by weight, for example, from about 0.7% to about 4%, or from about 1.0% to about 3%, relative to the total weight of the composition, including all ranges and subranges therebetween.

In various embodiments, the at least one polymeric filler is selected from Nylon-12, methyl methacrylated crosspolymer, and mixtures thereof and is present in an amount ranging from about 1% to about 3% by weight, such as about 2.5% by weight relative to the total weight of the cosmetic composition.

Liquid Fatty Ester (d)

The compositions of the invention comprise one or more liquid fatty esters.

The term "liquid fatty ester" means an ester that that is liquid at room temperature and atmospheric pressure (25° C., 1 atm) and which comprises in its structure at least one hydrocarbon-based chain containing at least 6 carbon atoms. Preferably, it has a melting point of less than or equal to about 10° C.

The liquid fatty esters may be esters of monoalcohols or of polyols with monocarboxylic or polycarboxylic acids, at least one of the alcohols and/or acids comprising at least one hydrocarbon-based chain containing at least 6 carbon atoms. Such liquid fatty esters are described, for example in US2012276029.

These liquid fatty esters may be glycerol esters and especially natural or synthetic mono-, di- or triglycerides, such as plant oils (non-volatile), for instance sunflower oil, corn oil, soybean oil, marrow oil, grape seed oil, pracaxi oil, argan oil, sesame oil, hazelnut oil, apricot oil, macadamia oil, arara oil, castor oil, avocado oil, jojoba oil or shea butter oil.

Preferably, the liquid fatty ester according to the invention is chosen from esters of a fatty acid (at least 6 carbon atoms) and of a monoalcohol, more particularly from esters of a fatty monoacid and of a monoalcohol. Preferably, at least one of the alcohols and/or acids is branched. Preferably, the alcohol and/or the acid are saturated, and preferentially both are saturated. Preferentially, the liquid fatty ester is not oxyalkylenated.

The liquid fatty esters according to the invention are preferably of formula

in which:
R1 denotes a linear or branched, saturated or unsaturated, optionally mono- or polyhydroxylated hydrocarbon-based radical, containing from 5 to 31 carbon atoms, preferably containing from 7 to 21 carbon atoms, and
R2 denotes a linear or branched, saturated or unsaturated, optionally mono- or polyhydroxylated hydrocarbon-based radical, containing from 1 to 20 carbon atoms.

Preferably, R1 denotes a linear or branched alkyl (saturated) radical containing 7 to 21 carbon atoms, especially from 8 to 17 carbon atoms, and more preferably from 8 to 15 carbon atoms.

Preferably, R2 denotes a linear alkyl (saturated) radical containing 1 to 4 carbon atoms or a branched alkyl (saturated) radical containing from 3 to 20 carbon atoms, especially from 3 to 16 carbon atoms. More preferably, R2 denotes a branched saturated alkyl radical containing from 3 to 12 carbon atoms.

Non-limiting examples of monoesters of monoacids and of monoalcohols useful in the invention include ethyl laurate, butyl laurate, hexyl laurate, isohexyl laurate, isopropyl laurate, isoamyl laurate, methyl myristate, ethyl myristate, butyl myristate, isobutyl myristate, isopropyl myristate, 2-octyldodecyl myristate, 2-ethylhexyl monococoate (or octyl monococoate), 2-ethylhexyl isononanoate, ethyl palmitate, isopropyl palmitate, isobutyl palmitate, 2-ethylhexyl palmitate (or octyl palmitate), butyl stearate, isopropyl stearate, isobutyl stearate, isocetyl stearate, isostearyl isostearate, isopropyl isostearate, 2-ethylhexyl stearate (or octyl stearate), 2-ethylhexyl hydroxystearate (or octyl hydroxystearate), decyl oleate, isononyl isononanoate, isodecyl neopentanoate, tridecyl neopentanoate, isocetyl neopentanoate, isostearyl neopentanoate, octyldodecyl neopentanoate and isoarachidyl neopentanoate, and mixtures thereof.

Preferably, the liquid fatty ester used in the invention is chosen from isodecyl neopentanoate, isononyl isononanoate, tridecyl neopentanoate, and mixtures thereof.

The compositions according to the invention comprise the said liquid fatty ester(s) in an amount ranging from 2% to 15% by weight, preferably from 5% to 12% by weight, preferentially from % to % by weight and better still from 7% to 10% by weight, relative to the total weight of the composition, and including all ranges and sub ranges there between.

Silicone Solvent (e)

The compositions of the invention also include at least one silicone oil or solvent.

The silicone oil preferably is a low viscosity oil, for example, an oil having a viscosity ranging from about 5 cSt to about 20 cSt, at approximately room temperature and pressure. In an embodiment, the silicone oil may be chosen from low viscosity dimethicones having a viscosity of about 5 cSt at approximately room temperature and pressure, and low viscosity dimethicones having a viscosity of about 20 cSt at approximately room temperature and pressure.

The low viscosity silicone oil preferably also is non-volatile. Such silicone oils include, for example, non-volatile polydimethylsiloxanes (PDMSs), polydimethylsiloxanes comprising alkyl or alkoxy groups, that are pendent and/or at the end of a silicone chain, wherein the alkyl or alkoxy groups each comprise from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates.

The silicone oil may be chosen from cyclic and linear organopolysiloxanes. Cyclic organopolysiloxanes may include, for example, cyclotetrasiloxane; cyclopentasiloxane; and methylated cyclic organopolysiloxanes, e.g., octamethylcyclotetrasiloxane and decamethylcyclopentasiloxane. Non-limiting examples of linear organopolysiloxanes include low molecular weight dimethicones; high molecular weight dimethicones; alkyl derivatives of linear organopolysiloxanes, e.g., cetyl dimethicone and lauryl trimethicone; aryl derivatives of linear organopolysiloxanes, e.g., phenyl trimethicone; and hydroxylated derivatives of linear organopolysiloxanes, e.g., dimethiconol.

In a particular embodiment, the silicone oil is selected from a phenyl trimethicone, such as the product DC 556 Cosmetic Fluid, and caprylyl methicone, such as the product FZ-3194, both which are available from Dow-Coning, and mixtures thereof.

The compositions according to the invention comprise the said silicone (s) in an amount ranging from 20% to 40% by weight, typically from 25% to 35% by weight, more typically from 27% to 32%, by weight, preferably from 28% to 31% by weight, relative to the total weight of the composition, and including all ranges and sub ranges there between.

Waxes (f) and (g)

The composition of the invention also includes at least two waxes, one wax having a melting point greater than or equal to about 70° C. and one wax having a melting point below about 70° C. The waxes may be natural or synthetic. Any of the waxes having the appropriate melting point and which are normally used in cosmetic products, particular foundations, may be used in this invention. The wax under consideration in the context of the present invention is generally a lipophilic compound that is solid at room temperature (25° C.). Additionally, waxes that are pliable as opposed to pasty or brittle are preferred.

Waxes with Melting Point Greater than or Equal to about 70° C. (f)

For ease of reference, the at least one wax having a melting point greater than or equal to about 70° C. is referred to herein as the "high melting point wax." This wax has a solid/liquid reversible change of state, having a melting point of greater than or equal to about 70° C., typically lower than about 80° C., most typically from about 71° C. to about 76° C. Examples of high meting point waxes that are suitable for the invention include in particular paraffins (within the higher melting point ranges) and ozokerite; polyethylene waxes, the waxes obtained by Fischer-Tropsch synthesis and waxy copolymers, and also esters thereof, fatty acids or esters obtained by catalytic hydrogenation of animal or plant oils containing linear or branched $C_8$-$C_{32}$ fatty chains, preferably $C_6$ to $C-l_8$ chains, silicone waxes and fluoro waxes, or a mixture thereof. The high melting point polyethylene wax may be chosen, for example, from homopolymers of ethylene and copolymers of ethylene and of another copolymerizable monomer corresponding to the following formula (I):

in which R can be chosen from linear and branched alkyl chains optionally interrupted by at least one unit chosen from mono- and polyoxyalkylenated units, aryl and aralkyl radicals, —$CH_2COOH$, and —$CH_2CH_2OH$.

Exemplary alkyl radicals may include methyl, ethyl, propyl, isopropyl, decyl, dodecyl and octadecyl radicals.

The mono- and polyoxyalkylenated units can include, for example, mono- and polyoxyethylene groups and mono- and polyoxypropylene groups.

The aryl radical can be, for example, chosen from phenyl and tolyl radicals.

The aralkyl radical can be, for example, chosen from benzyl and phenethyl radicals.

In an embodiment, the high melting point wax is chosen from natural waxes such as mineral, fossil, animal, and plant waxes, and hydrogenated oils that are solid, but still pliable, at 25 degrees centigrade. Representative natural waxes having a high melting point include ceresin wax, microcrystalline waxes, and ozokerite waxes.

In one embodiment, the high melting point wax is an ozokerite. Ozokerite is a fossil hydrocarbon having a complex composition corresponding to the solid residue from the evaporation of paraffin-rich petroleum. A commercial ozokerite is, for example, the product CEROZO BLANCHE E 626®, which is a mixture of $C_{20-50}$ hydrocarbons which is marketed by the company BARLOCHER. Another commercial Ozokerite is Ozokerite Wax SP 1020P, available from Strahl U Pitsch.

A wax that also may be used is a $C_{20}$-$C_{40}$ alkyl (hydroxystearyloxy)stearate (the alkyl group containing from 20 to 40 carbon atoms), alone or as a mixture. Such a waxes are commercially available under the names Kester Wax K 82 P and Hydroxypolyester K 82 P® (from the company Koster Keunen), as well as mixtures thereof.

In a particular embodiment the high melting point wax has a melting point between about 70° C. and about 80° C., such as Ozokerite Wax SP 1020P, available from Strahl U Pitsch.

In various embodiments of the invention, the high melting point wax is present in an amount less than or equal to 1%, such as from about 0.1% to about 1%, typically from about 0.20% to about 0.80%, more typically from about 0.5% to about 0.6%, by weight, based on the weight of the total composition.

It has been found that including the high melting point wax present in amounts equal or less than 1% affords the inventive compositions desired structure and consistency while still allowing for soft, silky texture without too much of an increase in viscosity. Not having a large increase in viscosity of the formula is important as such increase results in undesirable pilling of the formula (formation of little balls and clumps) during application to the skin.

Waxes with Melting Point Less than about 70° C. (g)

For ease of reference, the at least one wax having a melting point less than about 70° C. is referred to herein as the "low melting point wax". This wax has a solid/liquid reversible change of state, having a melting point of less about 70° C., typically less than 67° C., and in particular less than about 66° C. Preferably, these waxes have a melting point that is higher than about 55° C. These waxes are softer than high melting point wax (f).

Examples of low meting point waxes that are suitable for the invention, include especially of hydrocarbon-based waxes, for instance beeswax, lanolin wax, esparto grass wax, berry wax, shellac wax, and sumac wax, orange wax, lemon wax, and mixtures thereof.

Fatty acids obtained by catalytic hydrogenation of animal or plant oils containing linear or branched $C_8$-$C_{32}$ fatty chains, preferably $C_{-16}$ to $C_{-18}$ chains, may also be used as the low melting point wax.

Other low melting point waxes include silicone waxes, such as $C_{30-45}$ alkyl dimethicone; and fluoro waxes.

Esters obtained by catalytic hydrogenation of animal or plant oils may also be used. These include waxes obtained by hydrogenation of castor oil esterified with cetyl alcohol, sold under the names Phytowax ricin 16L64® and 22L73® by the company Sophim. Such waxes are described in patent application FR-A-2 792 190.

Other exemplary low melting point waxes include silicone wax. A non-limiting example of silicone was is C30-C45 alkyldimethylsilyl polypropylsilsesquioxane, one commercial example of which is Dow Corning® SW Resin Wax.

Beeswax, paraffin wax and isoparaffin wax are also useful.

Further examples of such waxes are provided in patent applications WO-01/13871 pages 9-10, WO-01/07007 page 29 or WO-00/74643 pages 26-29, the disclosures of which are incorporated by reference herein.

In particular embodiments, the at least one low melting point wax has a melting point between about 55° C. and about 67° C., preferably between about 60° C. and about 67° C. One such wax is beeswax.

In various embodiments of the invention, the low melting point wax is present in an amount from about 0.5% to about 2.5%, such as from about 1% to about 2.4%, typically from about 1.5% to about 2.3%, more typically from about 1.8% to about 2.2%, by weight, based on the total composition.

In particular embodiments, the total amount of waxes is less than about 4%, more typically less than about 3%. Use of low amount of waxes in the inventive compositions avoids formula opacity and assists in obtaining surety and uniformity of color.

Applicants have found that the ratio of the two waxes is significant to obtaining a formula that has proper structure, is not too thick and has good spreadability. In a particular embodiment, ratio of the high melting point wax to the low melting point wax is from about 0.4:1 to about 0.2:1, more particularly about 0.3:1.

Applicants have also found that the ratio of the amount of starch powders ((a)+(b)) to the amount of waxes ((f)+(g)) influences the spreadability of the formula (creamy), the fell and the unique ability of the formula transitioning from a crème texture to a powder text upon application. Thus, in a particular embodiment, the ratio of the total amount of starches to total amount of waxes ([(a)+(b)/(f)+(g)] is from about 15:1 to about 9:1, such as 13:1 to 10:1, including all ranges and sub-ranges therebetween, including particularly about 12:1. Formulas within these ratios have creamy spreadability, powdery feel upon application and an overall unique texture.

The Coloring Agent (h)

The cosmetic compositions disclosed herein further comprise at least one coloring agent.

Suitable coloring agents in accordance with various exemplary embodiments of the disclosure can produce, for instance, alone or as a mixture, a coloration having a yellow or orange hue. The coloring agents may, in certain embodiments, exhibit a significant reflectance in the range from about 550 to about 675 nm.

The at least one coloring agent may, for example, be chosen from mineral or organic pigments, coloring polymers, liposoluble dyes, organic lacquers, metallic powders, and mixtures thereof. A non-exhaustive list of suitable coloring agents can be found in the CTFA Cosmetic Ingredient Handbook, 11th Edition Cosmetic and Fragrance Association., Inc., Washington D.C. (2006).

Non-limiting examples of mineral coloring agents include yellow, red and brown metal oxides, for instance, iron oxides and titanium oxides. Metallic powders may include, for example, copper powders. The pigments FDC Yellow No. 5 (disodium salt of tartrazine) may be suitable as organic pigments. Examples of organic lacquers that are suitable for the invention include, for instance, FDC Yellow No. 5 and No. 6 A1 Lake.

The liposoluble dyes may be chosen, for example, from the brown dye identified by the Color Index number 12010; the yellow dyes identified, respectively, by the Color Index numbers 12700, 21230, 47000, 75125, 75135; the orange dyes identified by the Color Index numbers 11920, 40800, 40820, 40825, 40850, 45396, 75120, 75130 and capasanthine and the red dye identified by number 12150, and mixtures thereof.

A dyeing polymer is a polymer comprising at least one organic dye group. The dye group may be grafted, such as via covalent bonding, onto the chain of the polymer. The dye polymer may, in certain embodiments, contain less than about 10% by weight of dyestuff relative to the total weight of the polymer. The dye polymer may be of any chemical nature, such as polyester, polyamide, polyurethane, polyacrylic, poly (meth)acrylic, polycarbonate, of natural origin, for instance, cellulose or chitosan polymers, and mixtures thereof. In certain embodiments, the dye polymer may be a copolymer based on at least two different monomers, at least one of which is an organic dye monomer. Such dye polymers are described, for example, U.S. Pat. Nos. 5,032,670, 4,999,418, 5,106,942, 5,030,708, 5,102,980, 5,043,376, 5,104,913, 5,281,659, 5,194,463, and 4,804,719; International Patent Application Publication No. WO 92/07913; and European Patent Application Publication No. 0 747 036.

Non-limiting examples of dye polymer monomers include anthraquinones, methines, bis-methines, azamethines, arylidenes, 3H-dibenzo[7,i-j]isoquinolines, 2,5-diarylaminoterephthalic acids and esters thereof, phthaloylphenothiazines, phthaloylphenoxazines, phthaloylacridone, anthrapyrimidines, anthrapyrazoles, phthalocyanins, quinophthalones, indophenols, perinones, nitroarylamines, benzodifuran, 2H-1-benzopyran-2-one, quinophthalones, perylenes, quinacridones, triphenodioxazines, fluoridines, 4-amino-1,8-naphthalimides, thioxanthrones, benzanthrones, indanthrones, indigo, thioindigo, xanthene, acridine, azine, and oxazine.

The at least one coloring agent used in the compositions of the instant disclosure may be used in their raw form or may be pretreated, for example by way of surface-treatment. The aim of this treatment is generally to increase the stability of the color and to facilitate their incorporation into cosmetic formulations. In particular, coloring agents treated in order to make them hydrophobic will be more readily dispersible in an oily phase. By way of example, the coloring agent may be surface-treated with a hydrophobic and oil-repellant agent of the perfluoroalkyl phosphate derivative type, as described in EP 1 086 683. The coloring agents may also be surface treated with a material that makes them compatible with the oily phases, such as the silicone phases used in certain cosmetic formulations. Pigments of this type are described, for example, in U.S. Pat. No. 5,143,722.

Coloring agents suitable for use in accordance with the instant disclosure may include, but are not limited to, brown iron oxide and yellow iron oxide, optionally coated with perfluoroalkyl phosphate, and titanium oxide optionally treated with alumina and/or coated with perfluoroalkyl phosphate, such as the pigmentary pastes sold under the trade names Yellow Iron Oxide Covafluor, PF5 Yellow 601 (yellow) and PF5 Red R516L (red), PF 5 Black BL100 by the company Daito, and those sold under the trade names FA50DRF, FA50DYF, FA65DF and FA65 DBF by the company Kobo; ultramarine blue optionally coated with perfluoroalkyl phosphate, such as the product sold under the trade name PF 5 Ultramarine No. 801 by the company Daito; ultramarine blue coated with silica, such as the product Unipure Blue LC 686 by the company Sensient; the disodium salts of tartrazine and the aluminum lakes of Allura red on alumina sold by the company Noveon under the names FDC Yellow No. 6, A1 Lake and FDC Yellow No. 5 A1 Lake, and mixtures thereof.

Alternatively the coloring agent may be chosen from those treated with at least one amino acid, which may exhibit improved affinity for the skin for example, pigments from Miyoshi Kasei sold under the names NAI-C33-8001-10, NAI-C33-8001-10, NAI-C33-7001-10, and NAI-C33-9001-10.

In an embodiment the coloring agent is selected from iron oxides, titanium oxide, ultramarine blue (preferably treated with silica), and mixtures thereof. In a particular embodiment the iron oxides are selected from yellow iron oxide, red iron oxide, black iron oxide, and mixtures thereof.

It is within the ability of one skilled in the art to select the coloring agents and their amounts to adjust the color of the composition to create the desired effect, for example to adjust the bulk color of the composition and/or the color of the composition on the skin. Generally, the at least one coloring agent may be present in the composition in an amount ranging from about 5% to about 25% by weight, for example, from about 10% to about 20%, by weight, relative to the weight of the formula.

Other Fillers, Mattifiers, Etc. (Optional)

The compositions of the invention optionally may include fillers and mattifiers different for any discussed above. Such other fillers and mattifiers should not interfere with the properties of the composition.

Examples of such optional fillers that may be used in the compositions of the invention are mineral fillers. These fillers can include, for example, lamellar or nonlamellar, colorless or white mineral particles of any shape, such as spherical, platelet, or oblong particles. In certain embodiments, the mineral fillers may be chosen from mica, silica, hectorite, calcium sodium borosilicate, calcium aluminum borosilicate, precipitated calcium carbonate, magnesium carbonate, magnesium hydrogen carbonate, hydroxyapatite, hollow silica microspheres, glass or ceramic microcapsules, clay, quartz, natural diamond powder, and mixtures thereof.

Non-limiting examples of commercially available silica powders include the porous silica microspheres sold under the name Sunsphere® H51 and H33 by Asahi Glass; and the polydimethylsiloxane-coated amorphous silica microspheres sold under the names SA Sunsphere® H 33 and H53 by Asahi Glass.

According to various embodiments, the mineral filler may be chosen from silica powders, calcium sodium borosilicate, and mixtures thereof. An example of a commercial calcium sodium borosilicate is Luxsil Cosmetic Spheres available from Potters Industry.

Preferably, the composition does not contain kaolin, boron nitride, talc or silica beads as these may render the composition ashy.

When present, the additional fillers and mattifiers, such as mineral fillers may, in various exemplary embodiments, be present in the cosmetic compositions in an amount ranging from about 1% to about 15% by weight, for example, from about 2% to about 10%, or from about 5% to about 8%, by weight, relative to the total weight of the composition, including all ranges and subranges therebetween.

In various embodiments, the mineral filler is chosen from silica powders, calcium sodium borosilicate, and mixtures thereof, and is present in an amount ranging from about 5% to about 8% by weight relative to the total weight of the cosmetic composition.

Other Additives (Optional)

In addition, other cosmetic ingredients may be included in the compositions according to the disclosure. Such ingredients are known, and include but are not limited to humectants, emulsifiers, antioxidants, surfactants, preservatives, fragrances, thickeners or texturizers, fatty compounds, emollients, coalescents, and/or plasticizers. One of skill in the art will be able to select appropriate types and amounts of additional cosmetic ingredients based on, for example, the type of cosmetic composition being formulated and the desired properties thereof, and taking care not harm the properties of the compositions. When present, such additional cosmetic ingredients may be present in the compositions according to the disclosure in a combined amount ranging from about 10% to about 80%, such as about 15% to about 60%, about 25% to about 40%, or about 30% to about 35%, including all ranges and subranges therebetween.

Exemplary cosmetic compositions contemplated according to the disclosure include compositions are intended for application to a keratinous substrate, such as the skin. Such compositions are particularly suited for foundations.

By way of example only, foundation formulations described herein have been found to have one or more improved properties, such as improved oil absorption, shine reduction, matte, texture, and/or ability to impart true color, while also reducing dullness, whiteness, and/or ashiness of the skin. Moreover, the compositions allow for a transition from cream to powder upon application giving a nice powder feel to the skin and yet permit a smooth, creamy application.

Cosmetic Method

The instant disclosure also relates to a cosmetic method for making up and/or enhancing the appearance of a keratinous substrate, particularly skin, the method comprising applying to the keratinous substrate an anhydrous composition comprising, (a) at least one aluminum-based modified starch, (b) at least one acrylic starch, (c) at least one polymeric filler, (d) at least one liquid fatty ester, (e) at least one silicone solvent, (f) at least one wax having a melting point greater than 70° C., (g) at least one wax having a melting point less than 70° C., (h) a coloring agent, and (i) optionally a mineral filler, wherein the total amount of waxes ((f)+(g)) is less than about 5%.

All embodiments disclosed above with respect to the cosmetic compositions are equally applicable to the cosmetic method and are intended to fall within the scope of the disclosure.

According to one embodiment of the present disclosure, a cosmetic method for making up the skin, such as the facial skin, is provided. This method may, in certain embodiments, comprise the steps of loading an applicator, such as a sponge or pad, with a cosmetic composition disclosed herein, and applying said cosmetic composition onto the skin. In other embodiments, the user may apply the composition to the skin using the fingers. According to certain embodiments, the cosmetic composition may be applied to the skin more than once, such as twice or more, according to the cosmetic effect desired by the user.

The anhydrous cosmetic composition according to the invention may be packed in a cosmetic container delimiting at least one compartment which comprises the cosmetic composition, the container being closed by a closing member.

Method of Making

In an embodiment the invention relates to a method of making the above-described anhydrous cosmetic composition comprising the steps of:
1) making a pigment dispersion comprising pigments, silicone solvent and waxes;
2) adding to the pigment dispersion about ⅓ of the aluminum-based starch, and the aluminum-based starch and (met) acrylates polymer blend;
3) in a separate vessel making a homogenous slurry of about ⅔ of the aluminum-based starch, the fatty ester, and a small amount of silicone solvent; and
4) adding the slurry to the pigment dispersion and mixing until uniform.

The resulting composition was smooth (no clumps) and homogenous.

Container/Packaging

When the composition of the present invention is a foundation, the composition may be packaged in an applicator product comprising a reservoir and a removable cap for closing the reservoir. The cap may, for example, form a leak-tight seal.

The applicator assembly may also comprise a member for applying the composition to the face, wherein the applicator member allows the composition to be taken up and also allows the composition taken up to be applied to the face. This applicator member can be a flexible material, for example, a sponge or fibrous pad.

It is to be understood that both the foregoing description and the following Examples are exemplary and explanatory only, and are not to be interpreted as restrictive of the disclosure. Moreover, it should be understood that various features and/or characteristics of differing embodiments herein may be combined with one another. Other embodiments will be apparent to those skilled in the art from consideration of the disclosure and practice of the various exemplary embodiments disclosed herein.

Unless otherwise indicated, all numbers used in the specification and claims are to be understood as being modified in all instances by the term "about," whether or not so stated. It should also be understood that the precise numerical values used in the specification and claims form additional embodiments of the invention, and are intended to include any ranges which can be narrowed to any two end points disclosed within the exemplary ranges and values provided. Efforts have been made to ensure the accuracy of the numerical values disclosed herein. Any measured numerical value, however, can inherently contain certain errors resulting from the standard deviation found in its respective measuring technique.

EXAMPLES

The following Examples are intended to be non-restrictive and explanatory only, with the scope of the invention being defined by the claims.

TABLE 1

Sample Inventive Compositions: Cream To Powder Foundations

| Component (INCI) | Ex. 1* (% wt) | Ex. 2* (% wt) | Ex. 3* (% wt) |
| --- | --- | --- | --- |
| phenyl trimethicone (e) (DC 556 Cosmetic Fluid) | 30.5 | 30.5 | 30.50 |
| ozokerite wax (f) (Ozokerite Wax SP 1020 P) | 0.55 | 0.55 | 0.55 |
| beeswax (g) | 2.00 | 2.00 | 2.00 |

TABLE 1-continued

Sample Inventive Compositions: Cream To Powder Foundations

| Component (INCI) | Ex. 1* (% wt) | Ex. 2* (% wt) | Ex. 3* (% wt) |
|---|---|---|---|
| iron oxides pigments (h) | 20.0 | 20.0 | 17.13 |
| ultramarine blue (80%) (and) silica (20%) (h) | | | 0.70/0.17 |
| aluminum starch octenylsuccinate (a) (DryFlo Plus) | 28.45 | 28.45 | 28.45 |
| Aluminum starch octenylsuccinate (and) acrylates copolymer (and) magnesium carbonate (b) (Natrosorb HFB) | 1 | 1 | 1 |
| isodecyl neopentanoate (d) (DUB VC 10) | 8.0 | 8.0 | 8.0 |
| methyl methacrylate crosspolymer (c) (Techpolymer MBP-8) | 1.0 | 1.0 | 1.0 |
| calcium sodium borosilicate | 7.0 | 7.0 | 7.0 |
| Nylon-12 (c) (Orgasol 2002 EXD) | 1.5 | 1.5 | 1.5 |
| Total | 100 | 100 | 100 |
| Total wax | 2.55 | 2.55 | 2.55 |
| Total of (a)+(b) | 29.45 | 29.45 | 29.45 |
| [(a) + (b)]/waxes | 11.5:1 | 11.5:1 | 11.5:1 |
| wax (f)/wax (g) | 0.275:1 (about 0.3:1) | 0.275:1 (about 0.3:1) | 0.275:1 (about 0.3:1) |

*By active amount.

Method of Preparation:

The above compositions were prepared as follows:

1) In a main kettle, ⅝ of phenyl trimethicone and the waxes were combined and preheat to about 80-85° C.
2) The components of 1) were then mixed in a silverson while pigments were added. Mixing/grinding was continued for 1 hour. The pigment dispersion was checked under the microscope.
3) The pigment grind was moved to Rayneri mixer and mixing was continued with a normal mixing blade while temperature was maintained at about 85-90° C.
4) Approximately ⅓ of the aluminum starch octenylssuccinate powder and the aluminum starch octenylsuccinate (and) acrylates copolymer (and) magnesium carbonate were then added slowly one by one, making sure each was mixed in homogenously.
5) In a separate vessel, a slurry was made by combining the remaining phenyl trimethicone and isodecyl neopentanoate, heating to 80-85° C., then while mixing with a caframo mixer, steadily sifting in the remaining aluminum starch octenylsuccinate. Once the mixture was homogenous, it was added to the main kettle while mixing.
6) The methyl methacrylate crosspolymer, calcium sodium borosilicate and Nylon-12 were then added one by one and mixing was continued until homogenous.
7) The homogenous batch was then poured into containers that were at a temperature between 75-80° C. and allowed to cool to room temperature.

The resulting compositions were smooth and creamy, easy to apply and afforded even application. The compositions provided a nice matte finish, good oil control, evened skin tone and were not ashy on darker skin shades.

What is claimed is:

1. An anhydrous cosmetic composition comprising:
   (a) at least one aluminum-based starch;
   (b) at least one aluminum-based starch and (meth)acrylates polymer blend;
   (c) at least one polymeric filler;
   (d) at least one liquid fatty ester;
   (e) at least one silicone solvent;
   (f) at least one wax having a melting point greater than or equal to 70° C.;
   (g) at least one wax having a melting point less than 70° C. and being softer than (f);
   (h) at least one coloring agent; and
   (i) optionally a filler other than (c);
   wherein the total amount of waxes ((f)+(g)) is less than about 5%, by weight, relative to the total weight of the composition.

2. The composition of claim 1 comprising less than about 4% waxes, by weight, relative to the weight of the final composition.

3. The composition of claim 2 wherein the total amount of the aluminum-based starch (a) and the aluminum-based starch and (meth)acrylates polymer blend (b) is greater than about 20%.

4. The composition of claim 3 wherein the aluminum-based starch and (meth)acrylates polymer blend is less than about 1.5%, by weight, relative to the weight of the composition.

5. The composition of claim 4 wherein the amount of starch (a) plus starch/(meth)acrylates blend (b) to the total amount of waxes (f) plus (g) is from about 15:1 to about 9:1, including all ranges and sub-ranges therebetween.

6. The composition of claim 5 wherein at least one aluminum-based starch (a) is present in the composition in an amount from about 20% to about 35%, by weight, relative to the weight of the composition.

7. The composition of claim 6 wherein the at least one aluminum-based starch and (meth)acrylates polymer blend (b) is present in the composition in an amount from about 0.1% to less than about 1.5% by weight, relative to the total weight of the composition.

8. The composition of claim 7 wherein the at least one polymeric filler (c) is present in the composition in an amount from about 0.5% to about 6% by weight, relative to the total weight of the composition.

9. The composition of claim 8 wherein at least one liquid fatty ester (d) is present in the composition in an amount from about 2% to about 15% by weight, relative to the total weight of the composition.

10. The composition of claim 9 wherein at least one silicone solvent (e) is present in the composition in an amount from about 20% to about 50% by weight, relative to the total weight of the composition.

11. The composition of claim 10 wherein at least one wax having a melting point greater than or equal to 70° C. (f) is present in the composition in an amount less than about 1% by weight, relative to the total weight of the composition.

12. The composition of claim 11 wherein at least one wax having a melting point less than 70° C. (g) is present in the composition in an amount from about 0.5% to about 2.5% by weight, relative to the total weight of the composition.

13. The composition of claim 12 wherein ratio of the wax having a melting point greater than or equal to 70° C. (f) to the wax having a melting point less than 70° C. (g) is from about 0.4:1 to about 0.2:1.

14. The composition of claim 12 wherein at least one coloring agent (h) is present in the composition in an amount from about 5% to about 25% by weight, relative to the total weight of the composition.

15. The composition of claim 14 wherein the aluminum-based starch (a) is selected from aluminum starch octenyl succinate.

16. The composition of claim 15 wherein the at least one aluminum-based starch and (meth)acrylates polymer blend (b) is aluminum starch octenyl succinate and acrylates copolymer.

17. The composition of claim 16 wherein at least one polymeric filler (c) is selected from methyl methacrylate crosspolymer, Nylon-12, and mixtures thereof.

18. The composition of claim 17 wherein at least one liquid fatty ester (d) is selected from isodecyl neopentanoate, isononyl isononanoate, tridecyl neopentanoate, and mixtures thereof.

19. The composition of claim 18 wherein the at least one silicone solvent (e) is selected from phenyl trimethicone, caprylyl methicone, and mixtures thereof.

20. The composition of claim 19 wherein at least one wax having a melting point greater than or equal to 70° C. (f) is selected from ceresin wax, microcrystalline waxes, ozokerite waxes, and mixtures thereof.

21. The composition of claim 20 wherein the at least one wax having a melting point less than 70° C. (g) is selected from beeswax, paraffin wax, isoparaffin wax and mixtures thereof.

22. The composition of claim 21 wherein the coloring agent (h) is selected from iron oxides, ultramarine blue, and mixtures thereof.

23. An anhydrous cosmetic composition comprising:
(a) from about 22% to about 33%, by weight, of at least one aluminum-based starch;
(b) from about 0.5% to about 1.5%, by weight, of at least one aluminum-based starch and (meth)acrylates polymer blend;
(c) from about 1% to about 3%, by weight, of at least one polymeric filler;
(d) from about 5% to about 12%, by weight, of at least one fatty ester;
(e) from about 25% to about 35%, by weight, of at least one silicone solvent;
(f) from about 0.2% to about 0.8%, by weight, of at least one wax having a melting point greater than or equal to 70° C.;
(g) from about 1% to about 2.4%, by weight, of at least one wax having a melting point less than 70° C. and being softer than (f);
(h) from about 5% to about 25% of at least one coloring agent; and
(i) optionally a mineral filler other than (c);
wherein the total amount of waxes ((f)+(g)) is less than about 3% by weight, the total amount of starch (a) and blend (b) is greater than about 20%, and ratio of amount of starch (a) plus blend (b) to the amount of waxes (0 plus (g) is from about 12:1 to about 11:1; all weights and ratios being relative to the total weight of the composition.

24. A method of making up a keratinous substrate by applying to said substrate a composition according to claim 1.

25. The method of claim 24, wherein the cosmetic composition is a foundation and the keratinous substrate is skin.

* * * * *